United States Patent [19]

Alt et al.

[11] Patent Number: 5,637,744
[45] Date of Patent: Jun. 10, 1997

[54] BIS FLUORENYL METALLOCENES AND USE THEREOF

[75] Inventors: Helmut G. Alt; Konstantinos Patsidis, both of Bayreuth, Germany; M. Bruce Welch; Peter P. Chu, both of Bartlesville, Okla.

[73] Assignee: Phillips Petroleum Company, Bartlesville, Okla.

[21] Appl. No.: 457,566

[22] Filed: Jun. 1, 1995

Related U.S. Application Data

[60] Division of Ser. No. 73,023, Jun. 7, 1993, which is a continuation-in-part of Ser. No. 734,853, Jul. 23, 1991, Pat. No. 5,436,305, and a continuation-in-part of Ser. No. 984,054, Nov. 30, 1992, Pat. No. 5,393,911, which is a continuation-in-part of Ser. No. 697,363, May 9, 1991, Pat. No. 5,191,132, said Ser. No. 984,054, is a continuation-in-part of Ser. No. 697,363, May 9, 1991, Pat. No. 5,191,132.

[51] Int. Cl.$^6$ .................................................. C07F 17/00
[52] U.S. Cl. .................. 556/12; 556/28; 526/126; 526/127; 526/150; 526/160; 526/170; 526/943; 502/117
[58] Field of Search ............... 556/12, 28; 526/126, 526/127, 150, 160, 170, 943

[56] References Cited

U.S. PATENT DOCUMENTS

| | | | |
|---|---|---|---|
| 5,017,714 | 5/1991 | Welborn, Jr. ............... | 556/12 |
| 5,350,817 | 9/1994 | Winter et al. ............... | 526/119 |
| 5,436,305 | 7/1995 | Alt et al. ..................... | 526/160 |

FOREIGN PATENT DOCUMENTS

| 604908 | 6/1994 | European Pat. Off. . |
|---|---|---|
| 604917 | 6/1994 | European Pat. Off. . |

OTHER PUBLICATIONS

Resconi, et al., "High Molecular Weight Amorphous Polypropylene from Metallocene/MAO Catalysts", Polymer Preprints, 35(1), 663–664 (1994).

Spaleck, et al. "Stereorigid Metallocenes: Correlations Between Structure and Behaviour in Homopolymerizations of Propylene," *New J. Chem.*, 14, pp. 499–503 (1990).

Razavi, Dr. Abbas Paper, Electronic and Steric Influence of the Cyclopentadienyl Substituents and the Role of the Bridge on the Catalytic Behaviour of ANSA Metallocene Complexes in Stereospecific Polymerization of α–Olefin in Homogeneous Catalysis, SPO Conference (1992).

*Primary Examiner*—Romulo H. Delmendo
*Attorney, Agent, or Firm*—Edward L. Bowman

[57] ABSTRACT

Group IVB metal metallocenes of bis(1-methyl fluorenyl) diphenyl silane and bis(1-methyl fluorenyl) dimethyl tin are disclosed, plus their use in the production of polyolefins, including isotactic polypropylene.

5 Claims, No Drawings

BIS FLUORENYL METALLOCENES AND USE THEREOF

This application is a Division of application Ser. No. 08/073,023, filed Jun. 7, 1993 now pending, which is a continuation-in-part of U.S. application Ser. No. 07/734,853, filed Jul. 23, 1991, now U.S. Pat. No. 5,436,305, and a continuation-in-part of U.S. application Ser. No. 07/984,054, filed Nov. 30, 1992, now U.S. Pat. No. 5,393,911, which is a continuation-in-part of U.S. application Ser. No. 07/697,363, filed May 9, 1991, now U.S. Pat. No. 5,191,132, said Ser. No. 07/984,054 is a continuation-in-part of Ser. No. 07/697,363, now U.S. Pat. No. 5,191,132. The disclosures of the aforementioned copending applications and the patent are incorporated herein by reference.

FIELD OF THE INVENTION

The present invention relates to metallocenes. In another aspect, the present invention relates to the polymerization of olefins using metallocenes. In still another aspect, the present invention relates to novel olefin polymers prepared by polymerization using metallocenes. More particularly, the present invention relates to certain bridged bis(1-methylfluorenyl) sandwich-bonded metallocenes.

BACKGROUND OF THE INVENTION

It is well known that many metallocenes can be useful for the polymerization of some olefins. Particularly it has been noted that metallocenes can be combined with aluminoxanes to produce catalyst systems of high activity for the production of polyolefins. A particularly interesting type of metallocene for olefin polymerization is the so-called bridged sandwich-bonded metallocene in which the ligand of the metallocene comprises two cyclopentadienyl-like groups connected through a bridging group. Some of the bridged sandwich-bonded metallocenes when used in the polymerization of olefins having three or more carbon atoms have been found to be useful for producing polymers having different types of microstructure as reflected by tacticity determined by spectroscopic techniques such as infrared and NMR. A discussion of such techniques is disclosed in Zambelli et al, *J. Polym. Sci. Part C*, 84, 1488,(1962); Lotz et al, *Macro Molecules*, 21, 2375, (1988); Haftka et al, *J. Macromol. Sci. Phys.*, 830,319,(1991); and Youngman et al, *Macromol. Res.*, 2, 33 (1967).

It is well known in the art that the microstructure tacticity of a polyolefin molecule can have a significant effect upon the physical properties of the polymer. Other things which affect the polymer properties include the type of monomer, and comonomer if employed, the weight average molecular weight ($M_w$) of the polymer, the molecular weight distribution, and the composition distribution of the resin. Accordingly, for producing commercially desirable polymers, it is important to find metallocene catalysts which give the desired combination of polymer properties plus commercially practical polymerization activities.

Many sandwich-bonded bridged metallocenes have been at least proposed in the open literature and the patent literature and there have been some studies of the effects of varying the structure of the ligand used in the metallocene. One example of such a study is disclosed in the *New Journal of Chemistry*, Vol. 14, No. 6–7, pages 499–503 (1990). While the patent literature contains broad assertions regarding the particular types of polymers that will be produced with specific types of metallocenes, subsequent work has revealed that those generalizations are too broad.

For example, while U.S. Pat. Nos. 4,794,096 and 4,769,510 teach that bridged chiral, stereorigid metallocene catalysts are capable of producing polymers having high levels of isotactic microstructure, the only actual examples of such metallocenes are racemic ethylene bridged bisindenyl or bis-tetrahydroindenyl metallocenes which must be isolated from mixtures of the racemic and meso isomers by difficult, tedious, expensive fractional crystallizations or similar techniques. Further U.S. Pat. No. 4,892,851 shows that that the bridged, chiral, sterorigid metallocene cyclopentadienyl isopropylidene fluorenyl zirconium dichloride produces highly syndiotatic polypropylene rather than isotactic polyproplyene. Also Dr. Abbas Razavi in a paper at the SPO 92 meeting reported that the bridged, chiral, stereorigid metallocene racemic [bis(3-methyl indenyl) ethylene] zirconium dichloride yields a highly amorphous polypropylene rather than an isotactic polypropylene. The present inventors have also noted that certain bis-unsubstituted fluorenyl bridged metallocenes produce amorphous polypropylene having only low levels of isotaticity as determined by NMR.

An object of the present invention is to provide compositions comprising bis-fluorenyl bridged sandwich-bonded metallocene which are suitable for use in preparing isotatic polypropylene even without separation of racemic and meso isomers.

Another object of the present invention is to provide processes for polymerizing olefins using the special metallocene compositions.

In accordance with yet another aspect of the present invention, there is provided processes for producing novel isotactic polymers.

Other aspects, objects, and advantages of the present invention will become apparent from a review of the following disclosure.

SUMMARY OF THE INVENTION

In accordance with the present invention there is provided bis-fluorenyl bridged sandwich-bonded metallocene compositions suitable for producing polypropylene having significant isotatic content, the metallocenes are selected from the group consisting the sandwich-bonded metallocenes of metals of Groups IVB and the bridged ligands bis(1-methyl fluorenyl) diphenyl silyl and bis(1-methyl fluorenyl) dimethyl tin.

In accordance with yet another aspect of the present invention there is provided a method for polymerizing alpha olefins having at least three carbon atoms per molecule comprising contacting said olefin with the inventive bis-fluorenyl bridged metallocene compositions under suitable polymerization conditions.

In accordance with yet another aspect of the present invention there is provided the polymers produced from such polymerizations.

DETAILED DESCRIPTION OF THE INVENTION

Methods for the preparation of the bridged bis substituted fluorenyl compounds used in making the metallocenes are disclosed in the aforementioned U.S. Pat. No. 5,191,132 and in U.S. application Ser. No. 07/984,054. The term "fluorene" and the numbering of the substitutents thereof as used herein are used as defined in column 3 of that U.S. patent.

Methods for the preparation of the metallocene from the bridged bis(1-methyl fluorenyl) ligands are disclosed in the aforementioned copending application Ser. No. 07/734,853.

Typically in preparing the bis fluorenyl bridged ligands used in making the metallocenes 1-methyl fluorene is reacted with an alkali metal alkyl in a suitable liquid diluent to produce the 9-alkali metal salt of 1-methyl fluorene which is then reacted with a suitable precursor for the bridge to yield a composition containing the corresponding bridged bis-fluorenyl ligand which can then be reacted an alkyl metal alkyl to produce the divalent salt of the bis-fluorenyl ligand which is then reacted with a suitable transition metal compound to yield a metallocene composition.

The inventive metallocenes are suitable for producing polymers from alpha olefins and particularly for producing isotactic polymer from olefins having more than three carbon atoms. It is theorized that the level of the racemic isomer present when these metallocences are prepared is high enough that it is not necessary to separate it from the meso isomer in order to obtain substantially isotactic microstructure, or else that the meso isomer does not significantly affect the production of isotactic polymer.

The alkali metal alkyls employed for producing the anion salts of 1-methyl fluorene and the bridged bis(1-methyl fluorene) would typically be selected from sodium, potassium, and lithium alkyls having 1 to 8, more preferably 1 to 4 carbon atoms. Typically, the anion would be formed by dissolving or dispersing the fluorene compound in a suitable liquid diluent and then adding the alkali metal alkyl. Typically, in the past such techniques have used as the liquid diluent a polar solvent, for example, tetrahydrofuran. The present applicants have found that non-polar solvents, such as alkanes, cycloalkanes, aromatic hydrocarbons, and non-cyclic ethers can also be employed. Some specific examples include toluene, hexane, and diethyl ether. The resulting bridged bisfluorenyl ligand can be recovered and purified using conventional techniques known in the art such as filtration, extraction, crystallization, and re-crystallization. It is generally desirable to recover the ligand in a form that is free from any substantial by-product impurities. Accordingly, re-crystallization and fractional crystallization to obtain relatively pure ligand is often desirable. Dichloromethane has been found to be particularly useful for such re-crystallizations.

The inventive metallocenes can be prepared by reacting the di-alkali metal salt of the bridged bis fluorenyl-containing ligands with a suitable transition metal compound in a suitable liquid under suitable reaction conditions.

The term "transition metal compound" as used herein includes compounds of the formula $MeQ_k$ wherein Me is a metal selected from Group IVB metals of the Periodic Table. The currently preferred metals include titanium, zirconium, and hafnium. Each Q is individually selected from a hydrocarbyl radical, such as, for example aryl, alkyl, alkenyl, alkaryl, or arylalkyl radical having from 1 to 20 carbon atoms, a hydrocarbyloxy radicals having 1 to 20 carbons, or a halogen. Some non-limiting examples of such transition metal compounds include titanium tetrachloride, zirconium tetrachloride, hafnium tetrachloride, cyclopentadienyl zirconium trichloride, fluorenyl zirconium trichloride, 3-methylcyclopentadienyl zirconium trichloride, 4-methylfluorenyl zirconium trichloride, and the like. It is currently preferred to use inorganic transition metal halides.

The method of reacting the alkali metal salt of the bridged fluorenyl ligand with the transition metal compound is disclosed in commonly owned copending application Ser. No. 07/734,853, now U.S. Pat. No. 5,436,305. The molar ratio of the alkali metal alkyl to the fluorenyl radicals present in the ligand can vary, generally however, the ratio will be in the range of about 0.5/1 to about 1.5/1, still more preferably about 1:1. Typically, the alkali metal of the alkali metal alkyl would be selected from sodium, potassium, and lithium and the alkyl group would have from 1 to 8 carbon atoms, more preferably 1 to 4 carbon atoms. The molar ratio of the bridged fluorenyl ligand salt to the transition metal compound can also vary over a wide range depending upon the results desired. Typically, however, the molar ratio of the bridged fluorenyl compound to the transition metal compound is about 1:1.

The resulting metallocene can be recovered and purified using conventional techniques known in the art such as filtration, extraction, crystallization, and re-crystallization. Dichloromethane has been found to be particularly useful for such re-crystallizations. Since the stability of the various metallocenes varies, it is generally desirable to use the metallocenes soon after their preparation or at least to store the metallocenes under conditions favoring their stability, especially the tin bridged metallocenes. For example, the metallocenes can generally be stored in the dark at low temperature, i.e., below 0° C. in the absence of oxygen or water.

The reaction pressure and temperature for preparing the ligand and metallocene are not particularly critical and can vary over a wide range depending upon the results desired. Atmospheric pressures are currently preferred although higher and lower pressures could be employed. Typically, the reaction temperatures will be in the range of from about −100° C. to about 100° C. Generally, it is convenient to carry out the reactions at ambient temperatures in the range of about 15° C. to about 30° C.

The bis fluorenyl metallocenes of the present invention can be activated to produce a catalyst system suitable for the polymerization of olefin monomers. It is contemplated that the inventive fluorenyl silyl metallocenes can be activated using generally any of the techniques that in the past have been suitable for other similar metallocenes, including using cocatalyst or even activation using a stable non-coordinating counter anion such as disclosed in U.S. Pat. No. 5,155,080, e.g. using triphenyl carbenium tetrakis (pentafluorophenyl) boronate. In such processes, the metallocene or the co-catalyst can be employed on a solid insoluble particulate support.

Examples of typical co-catalysts include generally any of those organometallic co-catalysts which have in the past been employed in conjunction with transition metal containing olefin polymerization catalysts. Some typical examples include organometallic compounds of metals of Group IA, IIA, and IIIB of the Periodic Table. Examples of such compounds have included organometallic halide compounds, organometallic hydrides, and even metal hydrides. Some specific examples include triethylaluminum, triisobutylaluminum, diethylaluminium chloride, diethylaluminum hydride, and the like.

The currently most preferred co-catalyst is an aluminoxane. Such compounds include those compounds having repeating units of the formula

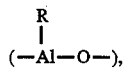

where R is an alkyl group generally having 1 to 5 carbon atoms. Aluminoxanes, also sometimes referred to as poly (hydrocarbyl aluminum oxides) are well known in the art and are generally prepared by reacting an organo hydrocarbylaluminum compound with water. Such a preparation techniques are disclosed in U.S. Pat. Nos. 3,242,099 and 4,808,561, the disclosures of which are incorporated herein by reference. The currently preferred co-catalysts are prepared either from trimethylaluminum or triethylaluminum, sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

The fluorenyl-containing metallocenes in combination with an aluminoxane co-catalyst can be used to polymerize olafins. Such polymerizations can be carried out in a homogeneous system in which the catalyst and co-catalyst are soluble; however, it is within the scope of the present invention to carry out the polymerizations in the presence of supported forms of the catalyst and/or co-catalyst in a slurry or gas phase polymerization. It is within the scope of the invention to use a mixture of two or more fluorenyl-containing metallocenes or a mixture of an inventive fluorenyl-containing metallocene with one or more other cyclopentadienyl-type metallocenes.

The fluorenyl-containing metallocenes when used with aluminoxane are particularly useful for the polymerization of mono-unsaturated aliphatic alpha-olefins having 2 to 10 carbon atoms. Examples of such olefins include ethylene, propylene, butene-1, pentene-1, 3-methylbutene-1, hexene-1, 4-methylpentene-1, 3-ethylbutane-1, heptene-1, octane-1, decene-1, 4,4-dimethyl-1-pantene, 4,4-diethyl-1-hexene, 3-4-dimethyl-1-hexene, and the like and mixtures thereof. The catalysts are also useful for preparing polymers of mixtures of ethylene and propylene or of ethylene and/or propylene and generally a minor amount, i.e. no more than about 12 mole percent, more typically less than about 10 mole percent, of a higher molecular weight olefin.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

Generally the molar ratio of the aluminum in the aluminoxane to the transition metal in the metallocene would be in the range of about 0.1:1 to about $10^5$:1 and more preferably about 5:1 to about $10^4$:1. As a general rule, the polymerizations would be carried out in the presence of liquid diluents which do not have an adverse affect upon the catalyst system. Examples of such liquid diluents include butane, isobutane, pentane, hexane, heptane, octane, cyclohexane, methylcyclohexane, toluene, xylene, and the like. The polymerization temperature can vary over a wide range, temperatures typically would be in the range of about −60° C. to about 280° C., more preferably in the range of about 20° C. to about 160° C. Typically the pressure would be in the range of from about 1 to about 500 atmospheres or greater. For particular results, it is sometimes useful to conduct the polymerizations in the presence of hydrogen.

A further understanding of the present invention and its objects and advantages will be provided by the following examples.

EXAMPLES

Example I

Preparation of bis-9-(1-methyl fluorenyl) diphenyl silane 1-methyl fluorene is dissolved in ether and mixed with a 1.6 molar solution of butyl lithium in hexane. The reaction was stirred at room temperature until the evolution of gas ceased. Then the solution was slowly added in the form of drops to a solution of diphenyl dichloro silane in ether. After the addition was complete, the mixture was stirred for one hour at room temperature and then hydrolyzed using saturated aqueous ammonium chloride solution. The organic phase was washed twice with 100 mL of water and then dried over sodium sulfate.

Example II

Preparation of bis-9-(1-methyl fluorenyl) dimethyl tin 3 gm of 1-methyl fluorene was dissolved in 100 mL of ether and mixed with 10.4 mL of a 1.6 molar solution of butyl lithium in hexane. After the evolution had ceased, 1.8 gm of dimethyl dichloro stannate in 150 mL of ether was slowly combined with the solution of 1-methyl fluorene. After the addition was complete, the mixture was stirred for an additional 4 hours at room temperature. After removal of the ether, the residue was eluted with dichloromethane and then the suspension was filtered over sodium sulfate in order to remove lithium chloride. The solution was concentrated by evaporation and the residue was washed with pentane.

Example III

Preparation of the Metallocenes

Metallocenes were prepared from the bridged ligands of Examples I and II. In each case, no attempt was made to separate the racemic isomer from the meso isomer. The corresponding ligand was dissolved in diethyl ether and mixed with two mole equivalents of butyl lithium supplied from a 1.6 molar hexane solution. After the evolution of gas had ceased, one mole equivalent of zirconium tetrachloride was added and the mixture stirred for 30 to 60 minutes. Then the solvent was removed and the residue extracted with methylene chloride and a suspension filter over sodium sulfate in order to remove lithium chloride which had formed. After concentrating the solution by evaporation, extraction was carried out with hexane followed by crystallization at −30° C. The purification can also be done by washing the crude product with diethylether in a soxhlett apparatus.

Example IV

Propylene Polymerization

Both of the metallocenes were separately evaluated for their effectiveness in the polymerization of propylene. The polymerizations were conducted in a 1 liter laboratory autoclave. In each case, a catalyst system was prepared by combining 1 mg of the metallocenes in 9 mL of toluene which was then mixed with 1 mL of a 30 wt. percent toluene solution of methyl aluminoxane obtained from Schering, Inc. and reported to have a weight average molecular weight of 900. The mixture was reacted until a change in color had occurred. Typically it was about 30 minutes at room temperature.

In the polymerization, 500 mL of propylene was first reacted with 10 mL of the methyl aluminoxane for 30 minutes at room temperature for drying purposes. The autoclave was then cooled to −10° C. and the catalyst solution was added from a pressure burette. The autoclave was then brought to 60° C. and held at this temperature for 60 minutes. At the end of the 60-minute period, the reactor was vented and the solid polymer recovered. This solid polymer in each case without further treatment was subjected to NMR analysis.

The polypropylene produced with the diphenyl silyl bridged metallocene exhibited a meso content of 89.53 and a racemic content of 10.47. The percent (mm), i.e. isotacticity was 84.1, the heterotacticity, percent (mr) was 10.9, and the syndiotacticity, i.e. percent (rr) was 5. The randomness index as compared to a Bernoullian randomness of 1 was 0.58. The average isotactic block length was 16.4. Size exclusion chromatography was used to determine the molecular weight distribution of the polymer. The weight average molecular weight was 180,000. The weight average molecular weight divided by the number average molecular weight was 3.

The dimethyl tin bridged bis(1-methylfluorenyl) metallocene yielded a polyolefin having a meso content, i.e. percent (m), of 86. Its isotacticity, i.e. percent (mm) was 78.5, the heterotacticity, i.e. percent (mr) was 14.9, and the syndiotacticity, i.e. percent (rr) was 6.6. The randomness index of the meso units compared to a Bernoullian index of 1 was 0.617. The average isotactic block length was 11.56.

That which is claimed is:

1. A bridged sandwich bonded metallocene of a Group IVB metal compound and a bridged ligand selected from the group consisting of bis(1-methyl fluorenyl) diphenyl silane and bis(1-methyl fluorenyl) dimethyl tin.

2. A metallocene according to claim 1 consisting of bis(1-methyl fluorenyl) diphenyl silyl zirconium dichloride.

3. A metallocene according to claim 2 wherein the metallocene consists essentially of the racemic isomer.

4. A metallocene according to claim 1 consisting essentially of bis(1-methyl fluorenyl) dimethyl tin zirconium dichloride.

5. A metallocene according to claim 4 wherein the metallocene consists essentially of the racemic isomer.

* * * * *